United States Patent
Klok et al.

(10) Patent No.: US 8,394,022 B2
(45) Date of Patent: Mar. 12, 2013

(54) SELECTIVELY PERMEABLE COATED MEMBRANE

(75) Inventors: Harm-Anton Klok, St-Sulpice (CH); Laurent Lavanant, Evian les Bains (FR)

(73) Assignee: Sensile Pat AG, Baar (CH)

( * ) Notice: Subject to any disclaimer, the term of this patent is extended or adjusted under 35 U.S.C. 154(b) by 1138 days.

(21) Appl. No.: 12/260,515

(22) Filed: Oct. 29, 2008

(65) Prior Publication Data

US 2009/0112075 A1 Apr. 30, 2009

(30) Foreign Application Priority Data

Oct. 30, 2007 (EP) .................................. 07021257

(51) Int. Cl.
*A61B 5/00* (2006.01)
(52) U.S. Cl. ........................................ 600/309; 600/365
(58) Field of Classification Search ........................ None
See application file for complete search history.

(56) References Cited

U.S. PATENT DOCUMENTS

| | | | |
|---|---|---|---|
| 5,164,427 A | 11/1992 | Wulff et al. | |
| 6,653,415 B1 | 11/2003 | Bottcher et al. | |
| 6,793,821 B2 | 9/2004 | Lee et al. | |
| 6,949,292 B2 | 9/2005 | Bottcher et al. | |
| 6,986,164 B1 | 1/2006 | Morales | |
| 2001/0035047 A1 | 11/2001 | Ehwald et al. | |
| 2004/0188351 A1 | 9/2004 | Thiele et al. | |
| 2005/0013988 A1 | 1/2005 | Fu et al. | |
| 2006/0009550 A1 | 1/2006 | Messersmith et al. | |
| 2006/0100493 A1 | 5/2006 | Strassler et al. | |
| 2006/0270922 A1 | 11/2006 | Brauker et al. | |
| 2007/0072220 A1 | 3/2007 | Chilkoti et al. | |
| 2008/0033269 A1* | 2/2008 | Zhang ........................... | 600/347 |

OTHER PUBLICATIONS

Ballarin et al. Chemical sensors based on ultrathin-film composite membranes—a new concept in sensor design. Analytical Chemistry 64:2647-2651 (1992).*
Schepelina et al. Polymer-filled opal nanopores. Langmuir 22:10523-10527 (2006).*
Xu et al. Functionalization of nylon membranes via surface-initiated atom-transfer radical polymerization. Langmuir 23:8585-8592 (2007).*
Cui et al. Synthesis of PNIPAM-co-MBAA Copolymer Nanotubes with Composite Control. Langmuir 22:8205-8208, published online Aug. 10, 2006.*
MSDS for N-isopropylacrylamide [online] [retrieved on Mar. 14, 2012] retrieved from http://www.sciencelab.com/msds.php?msdsId=9924411.*
MSDS for N,N'-methylenebisacrylamide [online] [retrieved on Mar. 14, 2012] retrieved from http://www.sciencelab.com/msds.php?msdsId=9926048.*
Jain et al. High-Capacity Purification of His-tagged Proteins by Affinity Membranes Containing Functionalized Polymer Brushes. Biomacromolecules 8:3102-7, published online Sep. 19, 2007.*
MSDS for acrylamide [online][retrieved on Mar. 16, 2012] retrieved from http://www.sciencelab.com/msds.php?msdsId=9927422.*

(Continued)

*Primary Examiner* — Samuel Woolwine
(74) *Attorney, Agent, or Firm* — Saliwanchik, Lloyd & Eisenschenk

(57) ABSTRACT

There is provided a selectively permeable biointerface membrane, permitting selective diffusion of analyte therethrough, for use in an analyte sensor comprising a nanoporous substrate and a coating, on the nanoporous substrate, comprising a plurality of polymer chains whereby each polymer chain is attached at one chain end thereof to a surface of the nanoporous substrate. There are also provided methods for the preparation of the selectively permeable membrane and an analyte sensor comprising the membrane.

29 Claims, 9 Drawing Sheets

OTHER PUBLICATIONS

Figure 1:
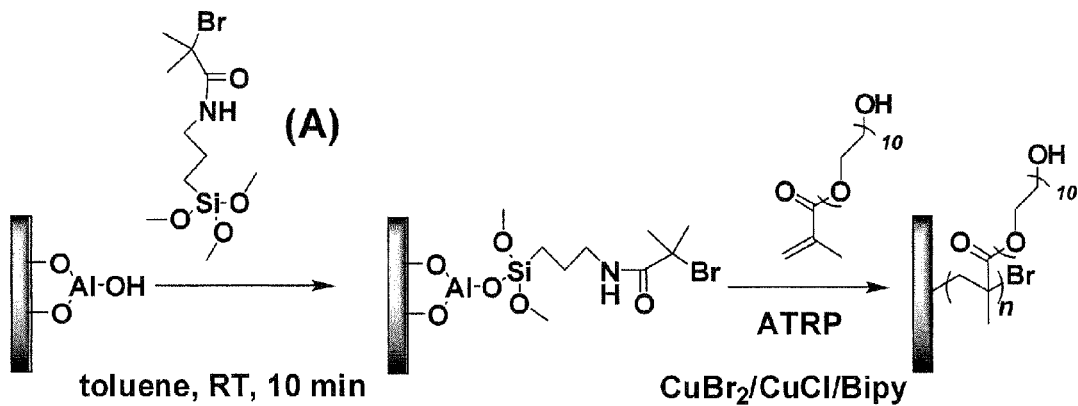
Figure 1:
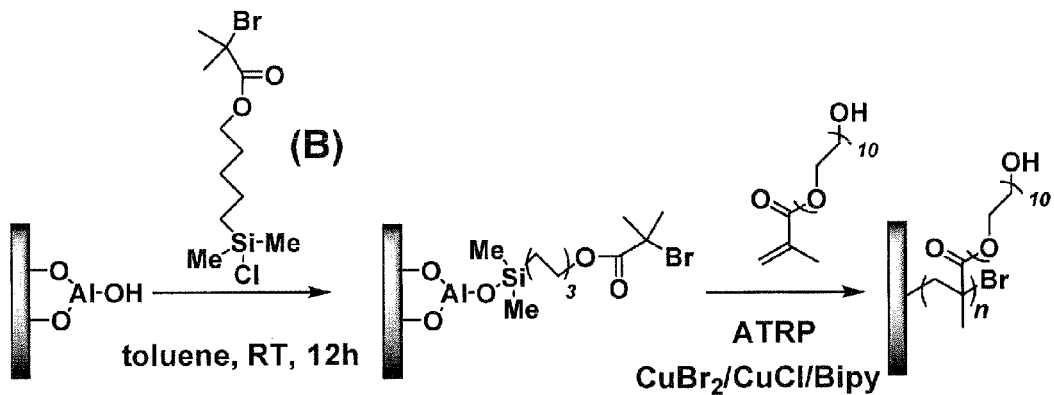
Figure 1:
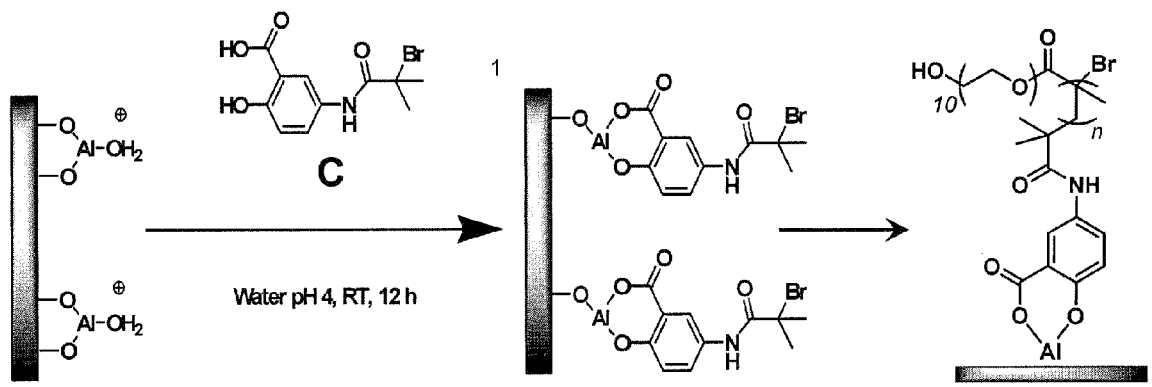

Sun et al. Polymer Brush Membranes for Pervaporation of Organic Solvents from Water. Macromolecules 38:2307-2314 (2005).*

Netrabukkana et al. Diffusion of Glucose and Glucitol in Microporous and Mesoporous Silicate/Aluminosilicate Catalysts. Ind Eng Chem Res 35:458-464 (1996).*

Mastrototaro et al. Preliminary Clinical Results from an Electroenzymatic Glucose Sensor Implanted in Subcutaneous Tissue. Proc Annual Int Conf IEEE Engineering Medicine Biology Society 14(1):154-5 (1992).*

Wisniewski et al. Methods for Reducing Biosensor Membrane Biofouling. Colloids and Surfaces B: Biointerfaces 18:197-219 (2000).*

Brown et al. Synthesis of oligo(ethylene glycol) methacrylate polymer brushes. European Polymer Journal 41:1757-65 (2005).*

* cited by examiner

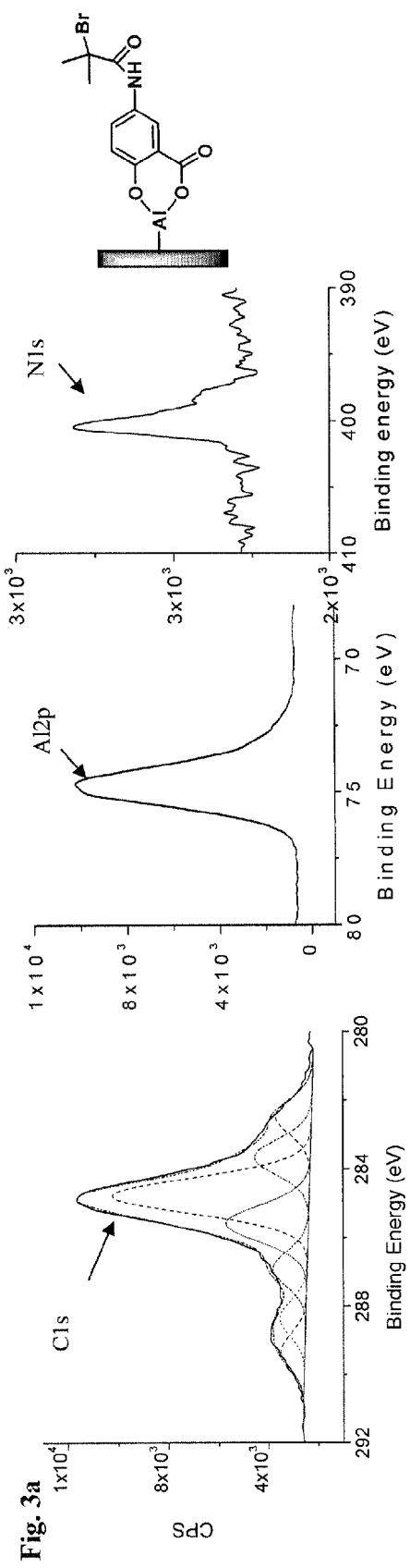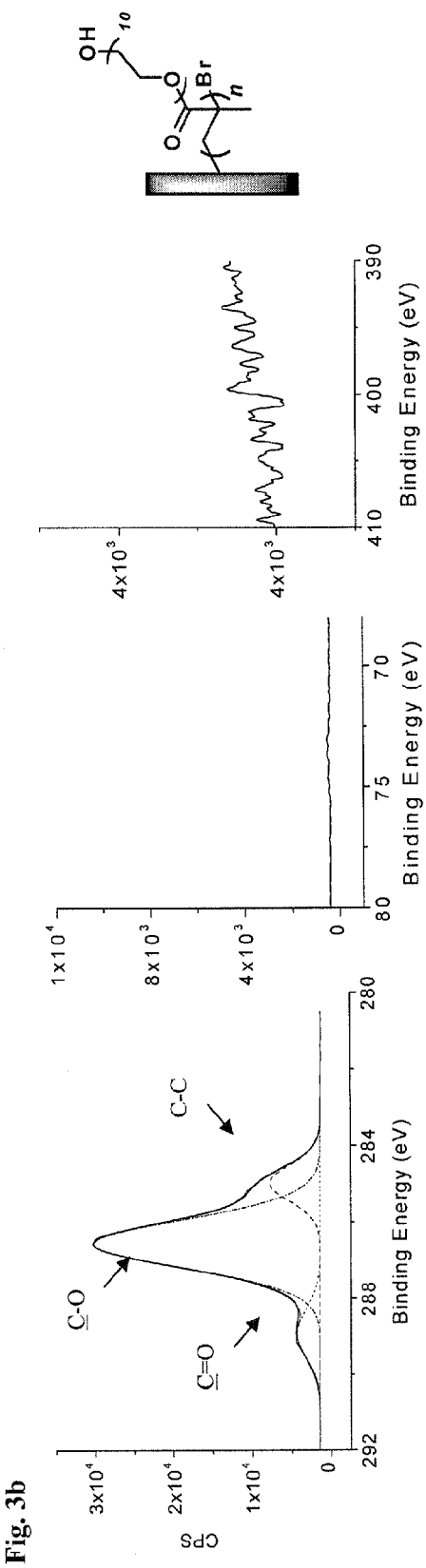
Fig. 3a
Fig. 3b

SELECTIVELY PERMEABLE COATED MEMBRANE

The present invention relates to the field of selectively permeable membranes more particularly to membranes permitting the selective diffusion of an analyte, to methods for the preparation of such membranes and to blood analyte sensor devices comprising the membranes.

Many fields of science require the monitoring of analyte concentrations in fluids, particularly in the medical field. For instance, in the treatment of insulin dependent diabetes patients must frequently monitor their blood glucose levels in order to appropriately manage insulin dosage. Without an accurate measurement of blood glucose levels there is the risk of inaccurate dosing of insulin with the associated dangers to the patient.

Various different medical devices have been proposed for the monitoring of blood glucose levels. Most conventionally used blood glucose monitors make use of chemical test strips which work on electrochemical principles. One drawback of such blood glucose monitors is that they require the patient to withdraw a drop of blood, for each measurement, generally requiring uncomfortable finger pricking methods. In order to avoid the pain caused by finger pricking and to allow more frequent, or continuous, control of glycaemia a variety of implantable sensors, including transdermal or subcutaneous sensors, are being developed for continuously detecting and/or quantifying blood glucose values. Semi-invasive, transdermal glucose sensors can provide a short term measuring solution (e.g. between one to seven days), however can suffer from problems of poor reliability and accuracy, especially in the hyperglycaemic range. Other problems relate to risks of infection at the skin-puncture site. Subcutaneous implanted glucose sensor devices have been proposed as a solution for long term, and continuous, glucose monitoring.

To date most interest in implantable glucose sensors has been directed to devices based on electro-chemical sensors comprising sensing electrodes covered by an enzyme layer including glucose oxidase and an outer bio-compatible coating. In the functioning of such sensors, glucose and oxygen diffuse into the enzyme layer of the membrane where they are consumed by the glucose oxidase producing gluconic acid and hydrogen peroxide. Glucose concentration is monitored by measuring the consumption of oxygen, the production of hydrogen peroxide or hydrogen ions, or PH variation.

Another type of implantable sensor system is based on mechanical sensing methods and uses affinity viscosimetry, whereby the concentration of affinity bindings is directly and mechanically measured, e.g. by measuring the viscosity of an analyte sensitive solution. This type of system allows accurate measurement of analyte concentration as the affinity bindings may be very specific, and moreover the analyte itself is not consumed as in electro-chemical analyte sensors.

One example of a transcutaneous viscosimetric affinity sensor is described in US 2001/0035047 A1. The sensor comprises a dialysis chamber section contained in a needle, into which glucose can penetrate, and a measurement chamber section located downstream of the needle. In operation new analyte sensitive liquid continuously flows from a reservoir through the dialysis chamber section (needle) and then through the measurement chamber section where the viscosity is determined.

An example of an analyte sensor for long-term implantation in the body, based on such mechanical sensing methods, is described in US 2006/0100493. The sensor, in the form of an ampoule, comprises a dialysis chamber containing a glucose sensitive liquid, comprising Concanavalin A (ConA) and dextran, into which glucose can penetrate through a selectively-permeable membrane. Glucose concentration is measured depending on the viscosity of the mixture consisting of the sensitive liquid and glucose using an oscillatory or rotational micro-viscometer.

Implantable analyte sensors, particularly subcutaneous analyte sensors for medium or long-term analyte monitoring, require bio-interface membranes that are bio compatible, e.g. that prevent non-specific adhesion of proteins, prevent fibrous encapsulation and promote vascularisation in the vicinity of the membrane.

A varying number of strategies for surface modifications of glucose sensors in order to combat the problems of foreign body reaction have been proposed. Membrane coatings based on hydrogels, phospho-lipids, nation, surfactants, diamond like carbon, naturally derived polymers and proteins have been investigated. Most of the surface modification methods investigated to date have been adapted to electro-chemical type bio-sensor electrode coatings. However the surface modification strategies proposed to date do not possess ideal characteristics with respect to foreign body reaction, coating long-term stability and analyte selective permeability.

It is an object of the present invention to provide a selectively permeable membrane for use in an analyte sensor which allows selective diffusion of analyte across the membrane, and which exhibits good bio-compatibility properties.

It would be advantageous to provide a membrane which allows selective diffusion of glucose across the membrane and simultaneously prevents transport of larger molecules such as peptides or proteins, or other potentially interfering molecules such as lactate or polysaccharide, contained in body fluids, across the membrane.

It would be advantageous to provide a membrane which exhibits good coating long-term stability properties.

Objects of the invention are achieved by an analyte sensor according to claim 1, and by a membrane according to claim 9.

There is now provided a selectively permeable biointerface membrane, permitting selective diffusion of analyte therethrough, for use in an analyte sensor, comprising a nanoporous substrate and a bio-compatible coating, on the nanoporous substrate, comprising a plurality of polymer chains whereby each polymer chain is bound at one chain end thereof to a surface of the nanoporous substrate. It is preferred that the polymer chains are covalently attached to a surface of the nanoporous substrate. The polymer chains attached at one chain end thereof to a surface of the substrate may alternatively be referred to as "polymer brushes". The polymer brush coating restricts the effective pore size of the pores of the nanoporous substrate, providing selective diffusion of analyte through the membrane.

Diffusion properties of the nanoporous substrate are controlled by the coating.

The polymer chains are preferably attached to the surface of the nanoporous substrate by a surface-initiated controlled/"living" polymerisation technique, by which the thickness, composition and density of the coating may advantageously be controlled.

The selectively permeable biointerface membrane of the present invention advantageously permits selective diffusion of analyte, for example glucose, fructose, galactose, maltose, in particular glucose, through the membrane and simultaneously prevents transfer of larger molecules and proteins across the membrane.

The substrate may be any suitable nanoporous substrate. Preferred substrates include nanoporous cellulose, alumina and polyethylene substrates. In an embodiment the substrate is nanoporous alumina.

The polymer brushes may be formed from homo-polymers or co-polymers of suitable water soluble monomers.

In a preferred embodiment the polymer chains are formed by a controlled/"living" radical polymerisation process, preferably by surface-initiated atom transfer radical polymerisation (SI-ATRP), from an initiator group covalently bound to the substrate surface.

Advantageously the use of a SI-ATRP process for the formation of the polymer brush coating from the nanoporous substrate surface allows the density of the polymer brush coating, i.e. the distance between polymer chains, as well as the thickness of the polymer brush coating layer to be accurately controlled.

There is also disclosed herein a salicylate initiator group for SI-ATRP processes, specifically a 5-(2-bromo-2-methyl-propanamido)-2-hydroxybenzoic acid initiator group.

According to a preferred embodiment, the polymer brushes are formed by ST-ATRP polymerisation of poly(ethyleneglycol) methacrylate (PEGMA) to form poly(poly(ethyleneglycol) methacrylate) (PPEGMA) polymer brushes.

Also provided herein is a method of preparation of a selectively permeable membrane for use in an analyte sensor, according to claim 9.

There is now provided an analyte sensor including a selectively permeable membrane, permitting selective diffusion of analyte therethrough, said membrane comprising a nanoporous substrate and a coating on the nanoporous substrate comprising a plurality of polymer chains, whereby each polymer chain is covalently attached at one chain end thereof to a surface of the nanoporous substrate.

The analyte sensor is advantageously a glucose sensor. Advantageously the sensor is based on mechanical sensing methods, sensing glucose diffused across the membrane. According to a preferred embodiment, the analyte sensor is an implantable glucose sensor comprising a dialysis chamber containing a glucose sensitive liquid and into which glucose can penetrate through the selectively permeable membrane. Glucose concentration is measured depending on the viscosity of the mixture consisting of the sensitive liquid and glucose. According to one embodiment viscosity is measured on the basis of the decay behaviour of an oscillating or rotating measuring element positioned in the sensitive liquid chamber, and excited by a driving magnet.

The selectively permeable membrane in the present invention advantageously allows diffusion of glucose into and out of the sensor and simultaneously prevents leakage of the molecular constituents of the sensitive solution out of the sensor, or of peptides or proteins into the sensor.

Further, the selectively permeable membrane of the present invention exhibits good bio-compatibility properties, showing advantageous low foreign body reaction properties. The good bio-compatibility properties of the membrane advantageously facilitate diffusion of glucose to the sensor device and permit long term, accurate and reliable, use of the sensor device.

Figure 2:
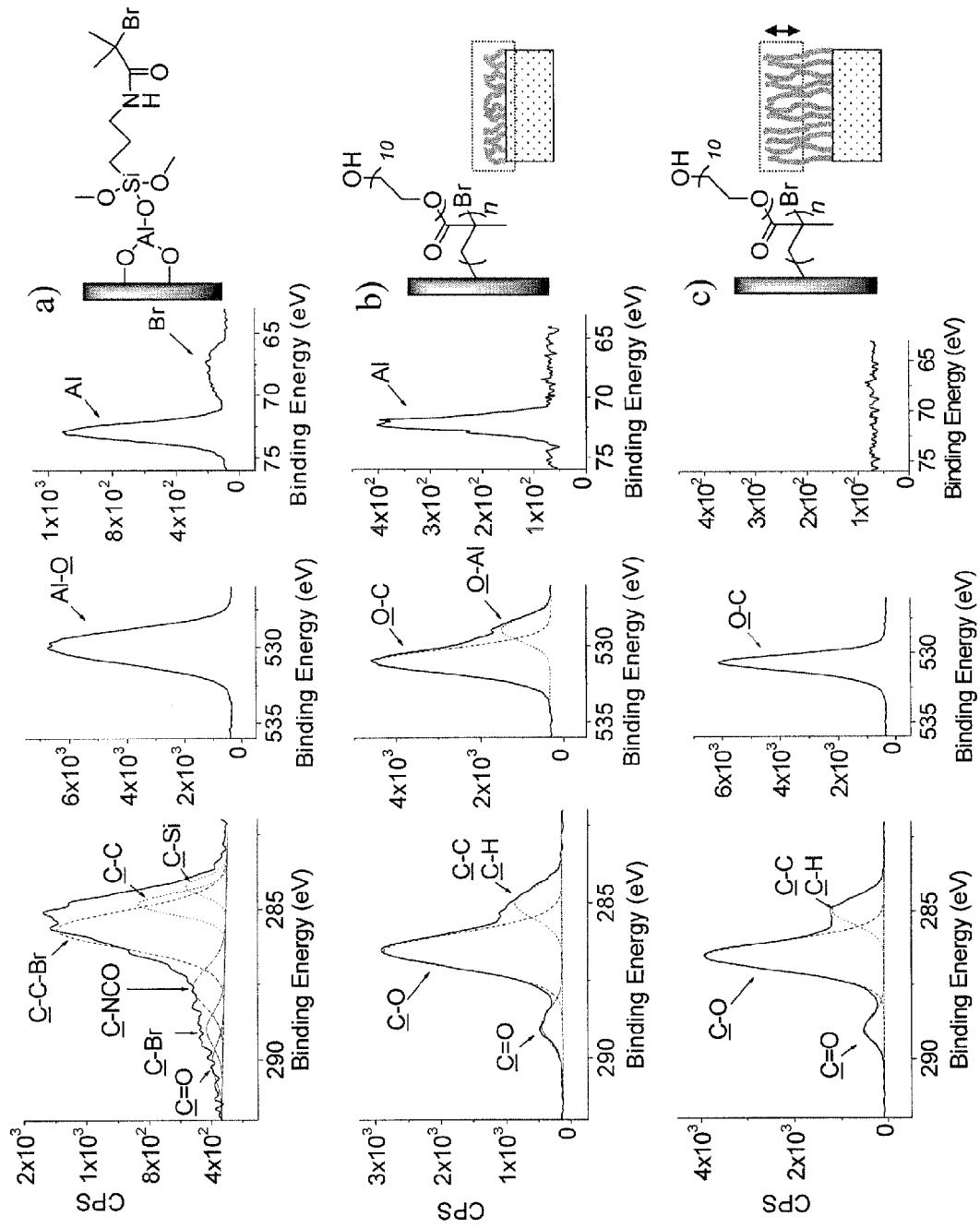
Figure 7:
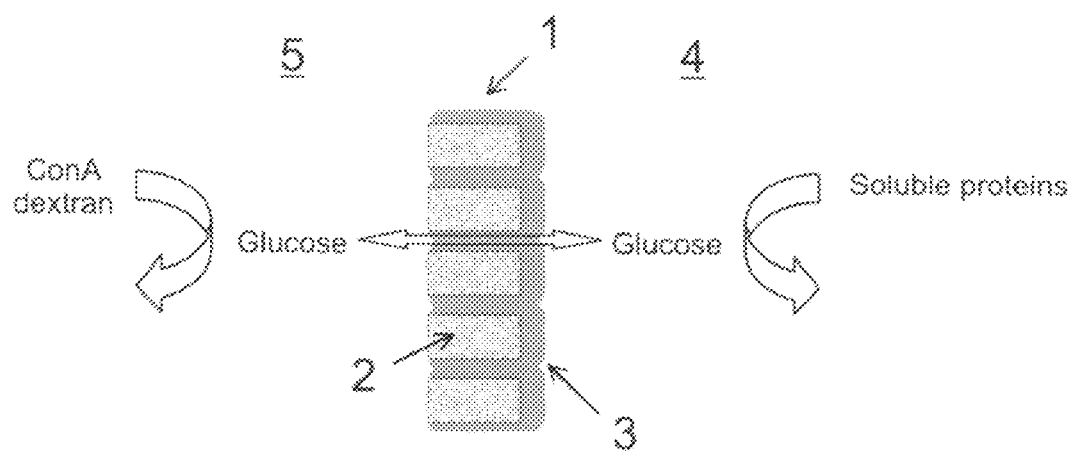

Further objects, advantageous features and aspects of the invention will be apparent from the claims and the following detailed description, and examples, in conjunction with the figures in which:

FIG. 1(*a*) shows a reaction scheme for the formation of the coated membrane according to an embodiment of the present invention;

FIG. 1(*b*) shows a reaction scheme for the formation of the coated membrane according to another embodiment of the present invention;

FIG. 1(*c*) shows a reaction scheme for the formation of the coated membrane according to another embodiment of the present invention;

FIGS. 2(*a*) to 2(*c*) show XPS spectra of a membrane according to an embodiment of the present invention;

FIGS. 3(*a*) and 3(*b*) show XPS spectra of a membrane according to another embodiment of the present invention;

FIGS. 4(*a*) and 4(*b*) show graphical representations of the glucose diffusion across coated membranes according to embodiments of the present invention;

FIG. 5 shows a graphical representation of the glucose diffusion behaviour across a coated membrane according to an embodiment of the present invention over time;

FIGS. 6(*a*) to 6(*d*) show optical micrographs of sections of implants of membranes according to embodiments of the present invention;

FIG. 7 shows a schematic illustration of mass transfer across a selectively-permeable membrane of an analyte sensor according to an embodiment of the present invention.

The nanoporous substrate may consist of any suitable porous material. Examples of nanoporous substrate materials include, for example metal oxides, silica, or polymeric substrates such as polyethylene, polypropylene, polyvinylidene difluoride (PVDF), polycarbonate, cellulose (regenerated cellulose, cellulose acetate, cellulose nitrate and cellulose ester), polyethersulfone (PES), nylon, TEFLON (PTFE). Particularly nanoporous alumina, cellulose or polyethylene substrates may be considered.

The pore size of the pores of the nanoporous substrate may generally vary between 2 and 800 nm, preferably pore size is not more than 200 nm. At a substrate pore size of above 200 nm the control of diffusion properties of the membrane substrate with the polymer brush coating layer tends to become less effective. A pore size of between 20 and 200 nm may be preferred.

A preferred substrate material is nanoporous alumina, e.g. produced by an anodization process. Alumina substrates have found acceptance for a wide range of bio-medical applications. Advantageously such nanoporous alumina substrates present a high porosity and a relatively uniform pore structure having substantially straight cylindrical pores of which the effective pore size may be well controlled by control of the characteristics of the polymer brush coating layer.

Commercially available nanoporous alumina membranes produced by anodic oxidization processes have a pore diameter dependent on the applied voltage, varying generally between 10 and 200 nm.

Another notable possible nanoporous substrate is nanoporous cellulose. Nanoporous cellulose membranes, e.g. re-generated cellulose, cellulose acetate or cellulose ester, are commercially available with pore sizes varying generally between 2 nm and 1000 nm. Nanoporous cellulose membranes find use as ultrafiltration membranes, e.g. in bioseparation techniques. Porous hollow fibres made of cellulose are also available. Nanoporous cellulose substrates are potentially suitable for the use in short-term, transcutaneous sensors. A drawback of such cellulose membranes is that their chemical and biological resistance is not suitable for use in a long-term implant.

The polymer of the polymer brushes as described herein may encompass any type of polymer, including homo-polymers, hetero-polymers, random co-polymers, block-co-polymer, ter-polymers, etc.

The polymer chains constituting the polymer brushes are, in general, formed by the polymerisation of any suitable monomer groups. Suitable monomers include water-soluble monomers susceptible to polymerisation via free radical polymerisation or controlled/"living" radical polymerization. Monomers should be non-toxic and non-immunogenic. Examples of suitable monomers for improved anti-biofouling properties include neutral monomers such as polyethylene glycol (PEG) and amphoteric phosphorylcholine containing monomers. PEG based monomers are particularly preferred due to the acceptance of PEG for pharmaceutical applications.

The monomeric units of the polymer chain may, for instance, comprise one or more monomer core groups having a bio-inert monomer side chain group coupled thereto, such that branched, or bristle-like, polymer brush polymer chains are formed on polymerisation; having a stem formed from the core groups and a plurality of branches formed from the side chain groups projecting from the stem. Suitable bioinert monomer head groups include polyethylene glycol, phosphorylcholine and carbohydrate. Suitable core monomeric groups include styrene, acrylonitriles, methacrylonitriles, acrylates, methacrylates, acrylamide, methacrylamides, vinyl, and combinations thereof.

Preferred monomer groups that may be homo- or co-polymerised to form the polymer brushes include 2-hydroxyethyl methacrylate, glycidyl methacrylate, (polyethylene glycol) methacrylate, (polyethylene glycol) methylether methacrylate, ethylene glycol dimethacrylate, poly(ethylene glycol) dimethacrylate.

In a preferred embodiment, the -polymer brush coating layer is comprised of poly(poly(ethylene glycol) alkylacrylate)) (PPEGAA), particularly poly(poly(ethylene glycol) methacrylate)) (PPEGMA) polymer chains.

In order to provide satisfactory stability properties and enhanced control over the polymer chain density, it is desired that the polymer brushes are created by covalent attachment methods. The attachment of the polymers to the substrate surface may be achieved by "grafting to" techniques which involve the tethering of pre-formed functionalized polymer chains to a substrate under appropriate conditions, or "grafting from" techniques which involve covalently immobilizing an initiator species on the substrate surface, followed by a polymerization reaction to generate the polymer brushes. Specific examples of grafting from techniques are surface-initiated controlled/"living" polymerisation techniques. Although other controlled surface-initiated polymerisation routes, such as cationic, anionic and ring-opening polymerisation (ROP) and ring-opening metathesis polymerization (ROMP) routes may be contemplated, preferred are controlled/"living" free radical polymerisation processes. Specific examples of controlled/"living" radical polymerisations are metal-catalysed surface initiated atom transfer radical polymerisation (SI-ATRP), stable free-radical polymerisation (SFRP), nitroxide-mediated processes (NMP), degenerative transfer processes, e.g. reversible addition-fragmentation chain transfer (RAFT), and photo iniferter mediated polymerization (PIMP) processes, amongst others. Advantages of the use of controlled/"living" free-radical polymerisation processes for polymer brush creation include enhanced control over the polymer brush layer thickness, high grafting density, control over the composition of co- or ter-polymer brushes, and the ability to prepare block co-polymers by sequential activation of a dormant chain end in the presence of different monomers.

In a preferred embodiment, the polymer brushes are created at the substrate surface by a controlled/"living" radical polymerisation process, preferably by surface-initiated atom transfer radical polymerisation (SI-ATRP). The SI-ATRP process is of particular interest due to its robustness and synthetic flexibility. Further, water may be used as the main solvent used for most SI-ATRP processes, which is a particular advantage for application on an industrial scale. The use of SI-ATRP processes for the creation of the polymer brush layer on the nanoporous substrate surface enables precise control over the thickness, polymer chain density, and composition of the polymer brush layer.

Surface initiated atom transfer radical polymerisation of monomers to form polymer brushes on the substrate surface can be carried out in accordance with known techniques, for example, such as described in a) Zhao, B.; Brittain, W. J. J. Am. Chem. Soc. 1999, 121, 3557-3558, b) Hussemann, M.; Malmstrom, E.; McNamara, M.; Mate, M.; Mecerreyes, D.; Benoit, D. G.; Hedrick, J. L.; Mansky, P.; Huang, E.; Russel, T. P.; Hawker, C. J. Macromolecules 1999, 32, 1424-1431, c) Matyjaszewski, K.; Miller, P. J.; Shukla, N.; Immaraporn, B.; Gelman, A.; Luokala, B. B.; Siclovan, T. M.; Kickelbick, G.; Vallant, T.; Hoffman, H.; Pakula, T. Macromolecules 1999, 32, 8716-8724, d) Ejaz, M.; Yamamoto, S.; Ohno, K.; Tsuji, Y.; Fukuda, T. Macromolecules 1998, 31, 5934-5926 for silicon wafers, such as described in von Werne, T.; Patten, T. E. J. Am. Chem. Soc. 1999, 121, 7409-7410 for silica, such as described in Sun, L.; Baker, G. L.; Bruening, M. L. Macromolecules 2005, 38, 2307-2314 for alumina, such as described in a) Shah, R. R.; Merreceyes, D.; Husemann, M.; Rees, I.; Abbott, N. L.; Hawker, C. J.; Hedrick, J. L. Macromolecules 2000, 33, 597-605, b) Kim, J.-B.; Bruening, M. L.; Baker, G. L. J. Am. Chem. Soc. 2000, 122, 7616-7617, c) Huang, W.; Kim, J.-B.; Bruening, M. L.; Baker, G. L. Macromolecules 2002, 35, 1175-1179 for gold, such as described in a) Fan, X.; Lin, L.; Dalsin, J. L.; Messersmith, P. B. J. Am. Chem. Soc. 2005, 127, 15843-15847, b) Zhang, F.; Xu, F. J.; Kang, E. T. Neoh, K. G. Ind. Eng. Chem. Res. 2006, 45, 3067-3073 for titanium oxide and such as described in Li, G.; Fan, J.; Jiang, R.; Gao, Y. Chem. Mater. 2004, 16, 1835-1837 for iron oxide, and as described in, for instance, U.S. Pat. No. 6,949,292, U.S. Pat. No. 6,946,164 and WO 98/01480.

Monomers capable of free radical polymerisation are advantageously styrene and its derivatives, acrylates, methacrylates and acrylonitrile, but also macromonomers and, in general, all compounds equipped with a C—C double bond capable of polymerisation. Different monomers may be used as a mixture, or one after another, in order to produce a co-polymer or block co-polymer on the substrate surface. The polymer chains formed on the surface substrate in the "living"/control free radical polymerisation reaction can be straight-chain or branched. Branched polymer chains may be preferred as providing improved properties for the restriction of the substrate pore size.

In general, in SI-ATRP processes, an initiator group is first chemically bound to the substrate surface, and then the living radical polymerisation carried out from the initiator in the presence of an appropriate catalytic system.

Dependent on the nature of the substrate material the substrate may exhibit chemical properties at its surface suitable for the binding of the initiator compounds, e.g. having reactive groups, such as hydroxide groups, on their surface. Reactive groups may also be introduced onto the surface of the substrate by exposure to chemicals, coroner discharge, plasma treatment, etc. For example, piranha solution or plasma treatment can be used to hydroxylate, or activate, the surface of a silica or alumina substrate.

The initiator group is covalently bound to the substrate surface via reactive groups present on the initiator group and at the substrate surface. The initiator group may be selected from known initiator groups. The choice of the initiator group for the ATRP polymerisation depends largely on the substrate material, the desired reaction conditions and the monomer(s) to be polymerised. Examples of suitable initiator species may be found, for example, in U.S. Pat. No. 6,949,292, U.S. Pat. No. 6,986,164, U.S. Pat. No. 6,653,415 and US2006/0009550A1.

The initiator molecules may be assembled onto the surface of the substrate in the presence of appropriate solvents.

Starting from the ATRP initiator bound to the substrate surface a "living"/controlled free radical polymerisation is carried out with the monomers capable of free radical polymerisation, as desired for the formation of the polymer brushes. The free radical polymerisation reaction is carried out in the presence of a suitable catalytic system. Typical catalytic systems comprise metal complexes containing transition metals e.g. copper, ruthenium or iron as the central metal atom. Exemplary metal catalysts include copper complexes such as copper chloride, copper bromides, copper oxides, copper iodides, copper acetates, copper perchlorate, etc.

In a particular embodiment, the PPEGMA polymer brush coating may be formed by SI-ATRP from a nanoporous metal oxide substrate, such as an alumina substrate, for example using a reaction scheme as illustrated in FIG. 1. The metal oxide substrate surface may first be treated in order to provide reactive groups on the substrate surface, for instance, an alumina substrate may be treated by a piranha treatment, or plasma treatment, to provide hydroxide groups on the alumina substrate surface.

An initiator species, for instance as described in U.S. Pat. No. 6,653,415, for example a bromoisobutyramido trimethoxysilane initiator group as shown in FIG. 1(a), or a chlorodimethylsilyl 2-bromo-2-methylpropanoate group as shown in FIG. 1(b), may be used. Other suitable initiator species include a cateholic alkyl halide initiator group, such as 2-Bromo-N-[2-(3,4-dihydoxy-phenyl)-ethyl]-propionamide, as described in US 2006/0009550.

According to a particular embodiment, the initiator species may be a salicylate initiator group, for example 5-(2-bromo-2-methylpropanamido)-2-hydroxybenzoic acid, as disclosed herein and shown in FIG. 1(c). It has been found that such salicylate initiator groups show an improved tendency to form surface complexes with metal oxide substrates, such as alumina. The use of such salicylate initiator groups advantageously allows the preparation of polymer brush coating on metal oxide substrates, e.g. alumina, having improved stability properties, particularly having good long-term stability.

In the case of a nanoporous regenerated cellulose substrate SI-ATRP may be carried out from the substrate surface using a suitable initiator capable of binding with hydroxyl groups on the cellulose substrate surface, for instance a 2-bromoisobutyryl bromide initiator group.

In a preferred embodiment, the polymer layer is formed by a "living"/controlled free radical polymerisation process, particularly SI-ATRP, of poly(ethylene glycol)methacrylate (PEGMA) to form a poly(poly(ethylene glycol methacrylate)) (PPEGMA) polymer brush coating. Formation of the PPEGMA polymer brush chains may be carried out from the initiator group by SI-ATRP using a suitable catalytic system, for instance a $CuCl/CuBr_2$/bipy catalytic system.

By the use of SI-ATRP to create the polymer brushes coating on the nanoporous substrate, the density and thickness of the polymer brush layer can be precisely controlled. The density of the polymer brushes may, for example, be controlled by controlling the density and coverage of the initiator group on the substrate surface. The thickness of the polymer coating produced in a specific SI-ATRP polymerisation reaction is controlled by the kinetics of the reaction which can be controlled in particular by controlling the length of time of the polymerisation reaction, or the concentration of monomers/catalyst.

By controlling the properties of the polymer brush coating layer on the nanoporous substrate, the diffusion properties of the alumina substrate may be modified. For instance, rate of analyte diffusion across the membrane, and the selective retention of larger molecules such as proteins, can be controlled by controlling the thickness of the polymer brush coating layer on the nanoporous substrate. The thickness of the polymer brush coating can be controlled in particular by controlling the length of time of the polymerisation reaction.

The polymer brush coating formed according to the present invention has the effect of pore-filling of the pores of the nanoporous substrate, that is to say a portion of the polymer chains at least partially fill the pores of the nanoporous substrate, thereby restricting the effective pore size of the nanoporous substrate. For instance the present invention enables the provision of membranes having a reduced effective pore size, e.g. of <10 nm, e.g. 1 to 5 nm, allowing selective diffusion of glucose and retention of larger molecules such as proteins, cells etc.

The thickness of the polymer brush coating on the nanoporous substrate required to provide the desired analyte selective diffusion properties will depend, amongst other things, on the nature and structure of the nanoporous substrate, the nature of the polymer brushes and the arrangement, e.g. density, of the polymer brushes on the substrate. As an example, a coating thickness of between 5 nm and 200 nm, for instance between 10 nm and 100 nm, e.g. between 20 nm and 60 nm, may be envisaged.

The coated membranes of the present invention show selective permeability properties permitting selective passage of analyte across the membrane and preventing transport of larger molecules such as proteins across the membrane.

Without wishing to be bound by any particular theory, it is considered that the polymer brushes grown on the nanoporous substrate form a mesh-like arrangement filling the pores of the nanoporous substrate, and that it is this mesh structure formed by the polymer chains in the pore network which provides the observed selective diffusion properties of the coated membrane.

Further the coated membranes of the present invention show good bio-compatibility, indicated by a very advantageous foreign body reaction. Advantageously the coated membranes of the present invention show good anti-biofouling properties in preventing protein and cell adhesion, and prevent fibrous encapsulation and promote vascularisation in the vicinity of the membrane.

Advantageously selectively permeable coated membranes of the present invention show good long term stability properties.

The selectively permeable membranes of the present invention having selective diffusion properties for allowing transport of analyte, particularly glucose, across the membrane and preventing leakage of larger molecules, such as proteins, together with the good bio-compatibility properties make the membranes of the present invention particularly advantageous for the use in implantable analyte sensor applications, including subcutaneous and transcutaneous analyte sensors.

Particularly, the coated membranes of the present invention are advantageously used in an implantable glucose sensor device.

The analyte sensor of the present invention is advantageously an affinity viscosimetry sensor. One embodiment of a glucose sensor comprising a semi-permeable coated membrane according to the present invention is an implantable sensor comprising a chamber containing a glucose sensitive liquid and a semi-permeable coated membrane, as described above, across which membrane glucose penetrates into the sensitive liquid. The viscosity of the sensitive liquid is measured as a measure of the glucose concentration.

The sensor works on the basis of measuring the change in viscosity of a glucose sensitive solution produced by the interaction of the sensitive solution with glucose entering the sensor. An exemplary sensitive solution comprises a mixture of dextran and Concanavalin A (ConA) in a physiological saline solution. The change of viscosity in dextran/ConA sensitive solution in the presence of glucose has been widely reported.

As illustrated in FIG. 7 the selectively permeable membrane (1) of the present invention, comprising a nanoporous substrate (2) and a biocompatible polymer brush coating (3) allows selective diffusion of glucose across the membrane (1) into and out of the sensor (5) such that the glucose concentration in the sensor is in equilibrium with the glucose concentration in the interstitial fluid (4) surrounding the sensor membrane, and simultaneously prevents leakage of dextran or ConA out of the sensor or proteins or other larger molecules into the sensor from the surrounding tissue.

Depending on the patient blood sugar level, more or less glucose diffuses through the semi-permeable membrane of the sensor into the sensitive solution, the diffusion properties of the membrane being such that the glucose level in the sensitive solution is in equilibrium with the glucose level in the surrounding interstitial fluid. The viscosity of the sensitive solution varies as a function of the glucose level such that measurement of the sensitive solution viscosity can be used to determine blood sugar level.

The glucose sensor may, for example, have a construction of a glucose sensor for long-term implantation as described in US 2006/0100493, and wherein the analyte sensor comprises an oscillating or rotating measuring element excited by a driving magnet, the viscosity of the mixture consisting of the sensitive liquid and glucose being measured on the basis of the decay behaviour of the oscillating or rotating measuring element after the driving magnet is switched off. Other constructions for the glucose sensor may be envisaged, such as a transcutaneous device wherein the dialysis chamber containing the glucose sensitive solution is presented in a needle section for insertion in a patient body.

Coated membranes according to the present invention have been shown to exhibit good glucose selective diffusion properties; showing good glucose diffusion rate across the membrane whilst retaining larger molecules, such as peptides and proteins, thereby advantageously enabling the provision of an implantable glucose sensor with a sufficiently fast glucose response time, whilst preventing transport of peptides, proteins and other larger molecules into the sensor, and ensuring no leakage of components of the sensitive solution out of the sensor.

The invention may be further illustrated by the following non-limiting examples.

EXAMPLES

Materials:
Commercially available anodic aluminum oxide membranes (ANOPORE from Whatmann) with a thickness of 60 µm and a quoted pore diameter of 20 nm, (sourced from Fisher Scientific).

Oligo(ethylene glycol)methacrylate (PEGMA) ~320 g·mol$^{-1}$ (PEGMA$_6$) and 526 g·mol$^{-1}$ (PEGMA$_{10}$) (sourced from Aldrich) and freed from the inhibitor by passing the monomer through a column of activated, basic aluminum oxide. 2,2'-Bipyridine (bipy), Cu (II) bromide (99.999%), Cu (I) chloride (purum, ≧97%), 2-bromo-2-methylpropionyl bromide, 5-amino salicylic acid and triethylamine (sourced from Aldrich), used as received.

3-(2-bromoisobutyramido)propyl(trimethoxy)silane (initiator A) synthesized as previously described [Ref: Tugulu, S.; Arnold, A.; Sielaff, I.; Johnsson, K.; Klok, H.-A. Biomacromolecules 2005, 6, 1602-1607].

6-(chlorodimethylsilyl)hexyl 2-bromo-2-methylpropanoate (initiator B) synthesized according to published protocol [Ref: Sanjuan, S.; Perrin, P.; Pantoustier, N.; Tran, Y. Langmuir 2007, 23, 5769-5778].

Example 1

Synthesis of PPEGMA Coated Nanoporous Alumina Membrane with
3-(2-bromoisobutyramido)propyl(trimethoxy)silane Initiator (Initiator A)

Synthesis of a PPEGMA$_{10}$ polymer brush coating was carried out from a nanoporous alumina substrate according to the reaction scheme illustrated in FIG. 1(a).

Nanoporous alumina membrane was washed with water, acetone and ethanol and then activated in a piranha solution (H$_2$O$_2$ (30 wt. % in H$_2$O)/H$_2$SO$_4$ (98 wt. %), 3:7 v:v), thoroughly rinsed with water and ethanol, dried in a stream of nitrogen and placed for 30 min. in a 2 mM solution of 3-(2-bromoisobutyramido)propyl(trimethoxy)silane (initiator A) in dry toluene at room temperature. The membranes were then rinsed extensively with anhydrous toluene, rinsed with water and acetone and dried in a stream of nitrogen.

Surface-initiated atom transfer radical polymerization of PEGMA$_{10}$ was carried out using a reaction system consisting of PEGMA$_{10}$, CuCl, CuBr$_2$ and bipy in the molar ratios: 1000:10:2:25. The polymerizations were performed in a water/methanol mixture (2:1/v:v).

78.1 mg (0.33 mmol) of CuBr$_2$ and 653.0 mg (4.20 mmol) of bipy were dissolved in a mixture of 80 mL of PEGMA$_{10}$ (167.00 mmol), 64 mL of water and 32 ml of methanol. After degassing by three freeze-pump-thaw cycles, 165.3 mg (1.67 mmol) of CuCl was added. Degassing was continued for 2 cycles. The resulting solution was subsequently transferred via a cannula to a nitrogen purged reaction vessel containing the activated alumina membrane and the reaction was allowed to proceed with stirring at 60° C. for the defined reaction time, between 10 minutes and 3 hours. The membrane was removed from the reactor and extensively washed with water, acetone and ethanol to remove residual physisorbed monomers/polymers and was finally stored in ethanol.

The membrane was analysed for grafting of the ATRP initiator A and of the PPEGMA$_{10}$ brushes by X-ray photoelectron spectroscopy (XPS). XPS was carried out using an Axis Ultra instrument from Kratos Analytical.

The C1s (carbon), O1s (oxygen) and Al2p (aluminum) core-level XPS spectra of nanoporous alumina membranes, a) grafted with the ATRP initiator, b) with PPEGMA$_{10}$ brushes obtained after 10 minutes of polymerisation and c)

with PPEGMA$_{10}$ brushes obtained after 3 hours of polymerisation are shown in FIGS. 2a), b) and c) respectively.

The C1s core-level spectrum of nanoporous alumina membranes grafted with the PPEGMA$_{10}$ brushes can be curve-fitted with three peak components at 285.0 eV, 286.5 and 289.0 eV respectively, which are attributed to aliphatic backbone (C—C/C—H), ethylene glycol units (C—O) and to the ester groups (C=O—O) of the polymer brushes [Ref: Xu, F. J.; Zhong, S. P.; Yung, L. Y. L.; Kang, E. T.; Neoh, K. G. Biomacromolecules 2004, 5, 2392-2403].

After 10 min of polymerization, the Al2p signal attributed the alumina substrate is still present and disappears after 3 h of polymerization. Assuming an XPS sampling depth of ~10 nm for common organic substrates [Ref: K. L. Tan, L. L. Woon, H. K. Wong, E. T. Kang and K. G. Neoh, Macromolecules, 1993, 29, 2832] it is therefore considered that the PEGMA$_{10}$ brushes reach a minimum thickness of 10 nm after 3 hours of polymerization (i.e. since the thickness of the PEGMA$_{10}$ brushes after 3 hours of polymerization is sufficient to screen the photoemission of electrons from the alumina surface).

Attenuated total reflectance Fourier transform infrared (ATR-FTIR) spectroscopy was carried out on a Nicolet Magna-IR 560 spectrometer equipped with a Specac Golden Gate single reflection diamond ATR system. Each spectrum was collected by accumulating 1280 scans at a resolution of 4 cm-1. ATR-FTIR spectra of the PPEGMA$_{10}$ brushes show a broad band at 1728 cm$^{-1}$ attributed to C=O vibrations, which confirms the presence of PPEGMA$_{10}$ brushes.

Advancing contact angle measurements were carried out using a DataPhysics OCA 35 contact angle measurement instrument. The presence of PPEGMA$_{10}$ brushes on the alumina substrates is also reflected in the drop of the advancing water contact angle from 14°±4° for alumina grafted with initiator A to 44°±4 for alumina grafted with PPEGMA$_{10}$ brushes surface. After 20 min of ATRP, a constant water contact angle is achieved which indicates that the surfaces are covered by PPEGMA brushes.

Example 2

Synthesis of PPEGMA Coated Nanoporous Alumina Membrane with 6-(chlorodimethylsilyl)hexyl 2-bromo-2-methylpropanoate Initiator (Initiator B)

Synthesis of a PPEGMA$_{10}$ polymer brush coating was carried out from a nanoporous alumina substrate according the reaction scheme illustrated in FIG. 1(b).

Nanoporous alumina membranes were cleaned using a microwave plasma stripper (Tepla 300, Microwave plasma stripper). This device produces soft plasma induced by microwave (power from 200 to 1000 W). Prior to the plasma treatment the membranes were cleaned with ethanol. The membranes were then introduced into the Tepla chamber, supported on a quartz stand, and subjected to a three step plasma cleaning process. In the first step, the Tepla chamber was evacuated. The oxygen plasma treatment was then initiated with a constant oxygen flow of 400 ml/min, and the plasma allowed to process for 1 min with a microwave power of 500 W. In the last step the chamber was evacuated in order to remove all trace of the burnt organics compound.

After cleaning the nanoporous alumina membranes were immersed in a 5 mM solution of 6-(chlorodimethylsilyl)hexyl 2-bromo-2-methylpropanoate (initiatorB) in dry toluene. The reaction was allowed to process overnight. The resultant membranes were washed with toluene and dried under nitrogen. Surface-initiated atom transfer radical polymerization of PEGMA$_{10}$ was carried from the initiator B coated alumina membranes as described in Example 1 above to form the PPEGMA$_{10}$ polymer brush coated membranes.

Example 3

Synthesis of PPEGMA Coated Nanoporous Alumina Membrane with 5-(2-bromo-2-methylpropanamido)-2-hydroxybenzoic Acid Initiator (Initiator C)

Synthesis of 5-(2-bromo-2-methylpropanamido)-2-hydroxybenzoic acid (initiator C) was carried out as follows:

To a suspension of 5-amino-2-hydroxybenzoic acid (3.0 g, 19.6 mmol) in a solution of freshly distilled triethylamine (4.1 mL, 29.4 mmol, 1.5 eq.) in 100 mL of anhydrous toluene was added dropwise 2-bromoisobutyryl bromide (6.8 mL, 53.8 mmol). Addition was performed at 0° C. under inert atmosphere. The mixture was then refluxed for 15 hours. Volatiles were removed under vacuum leaving oily crude materials. The product initiator C was extracted with ethanol concentrated and crystallized at −30° C. Yield: 30%. Analysis: $^1$H NMR (CDCl$_3$, 300 MHz, 298 K): δ 9.81 (s broad, 3H, NHCO and OH), 8.24 (s, 1H, Hortho), 7.76 (d, $^1$J=10.5 Hz, 1H, Hmeta), 6.82 (d, $^1$J=9.8 Hz, 1H, Hpara), 2.10 (s, 6H, Me). $^{13}$C NMR (CDCl3, 125 MHz, 298 K): δ 170.6 (CO—N), 167.2 (CO—O), 160.0 (C(aromatic)-OH), 130.8 (C(aromatic)-NH), 124.1 (C(aromatic)-H), 122.2 (C(aromatic)-H), 118.6 (C(aromatic)-H), 114.2 (C(aromatic)-CO$_2$H), 58.9 (C—Br), 33.6 (CH$_3$), confirming the product to be 5-(2-bromo-2-methylpropanamido)-2-hydroxybenzoic acid initiator (initiator C).

Synthesis of a PPEGMA$_{10}$ polymer brush coating was carried out from a nanoporous alumina substrate according the reaction scheme illustrated in FIG. 1(c).

The nanoporous alumina membranes were incubated overnight at pH=5 and ionic force I=0.01 mM (NaCl). After incubation, the membranes were immersed in a 5 mM solution of initiator C (C is first dissolved in 100 μl of acetone) in water (pH=5 and I=0.01 mM). After adding the ATRP initiator C, the pH decreases to pH=4. The reaction was allowed to process overnight. The slides were washed with water (pH=5 and I=0.01 mM) and were used immediately. Surface-initiated atom transfer radical polymerization of PEGMA$_{10}$ was carried from the initiator C coated alumina membranes following the method described in Example 1 above to form the PPEGMA$_{10}$ polymer brush coated membranes.

The membrane was analysed for grafting of the ATRP initiator C and of the PPEGMA$_{10}$ brushes by XPS, ATR-FTIR and advancing water contact angle as in example 1 above.

The C1s (carbon), O1s (oxygen) and Al2p (aluminum) core-level XPS spectra of nanoporous alumina membranes, a) grafted with the ATRP initiator C and b) with PPEGMA$_{10}$ brushes obtained after 120 minutes of polymerisation are shown in FIGS. 3a) and b) respectively.

The C1s core-level spectrum of nanoporous alumina membranes grafted with the PPEGMA$_{10}$ brushes can be curve-fitted with three peak components at 285.0 eV, 286.5 and 289.0 eV respectively, which are attributed to aliphatic backbone (C—C/C—H), ethylene glycol units (C—O) and to the ester groups (C=O—O) of the polymer brushes [Ref: Xu, F. J.; Zhong, S. P.; Yung, L. Y. L.; Kang, E. T.; Neoh, K. G. Biomacromolecules 2004, 5, 2392-2403].

After 120 min of polymerization, the Al2p core-level spectra shows the disappearance of the signal attributed to the alumina substrate. Assuming an XPS sampling depth of ~10 nm for common organic substrates [Ref: K. L. Tan, L. L.

Woon, H. K. Wong, E. T. Kang and K. G. Neoh, Macromolecules, 1993, 29, 2832] it is therefore considered that the PPEGMA$_{10}$ brushes reach a minimum thickness of at least 10 nm after 120 minutes of polymerization (i.e. since the thickness of the PEGMA$_{10}$ brushes after 120 minutes of polymerization is sufficient to screen the photoemission of electrons from the alumina surface).

Attenuated total reflectance Fourier transform infrared (ATR-FTIR) spectroscopy was carried as in Example 1. ATR-FTIR spectra of the PPEGMA$_{10}$ brushes showed broad bands at 3625-3160 cm$^{-1}$ and at 1728 cm$^{-1}$, attributed to O—H and C=O stretching vibrations, which confirms the presence of PPEGMA$_{10}$ brushes.

The presence of PPEGMA$_{10}$ brushes on the alumina substrates was also reflected in the drop of the advancing water contact angle from 10°±2° for non-treated alumina to 44°±4 for alumina grafted with PPEGMA$_{10}$ brushes surface. After 20 min of ATRP, a constant water contact angle is achieved which indicates that the surfaces are covered by PPEGMA brushes.

Example 4

Permeability Experiments

The ability of the PPEGMA coated alumina membranes prepared according to Examples 1 and 3 to allow selective passage of glucose and prevent transport of albumin, as a model protein, was evaluated.

The glucose diffusion and the albumin leakage/retention was tested using a test cell with two compartments, having a volume of 1.18 ml, separated by a PPEGMA coated or a non-coated porous alumina membrane.

For the glucose diffusion evaluation an aqueous solution containing 100 mM-D-glucose in ultrapure water was filed in one compartment and a reference solution (ultrapure water) was filled in the second compartment. The test cell was set on a mini-shaker with the agitation speed of 700-750 rpm to provide mixing of the aqueous solution in each compartment of the test cell in order to reduce the influence of the boundary condition at the liquid-membrane interface. The variation of glucose concentration in the second compartment was measured by refractometer equipped with a temperature compensation function (RFM 342; Bellingham and Stanley Ltd). For each glucose concentration measurement 60-70 μl of liquid was extracted form the second chamber and the glucose concentration measured by refractometer.

Example 4(A): The diffusion of glucose and albumin across alumina membrane substrates with PPEGMA polymer brush coating of thicknesses of 17 nm, 27 nm, 37 nm and 75 nm, produced according to Example 1, were evaluated.

Figure 4A:
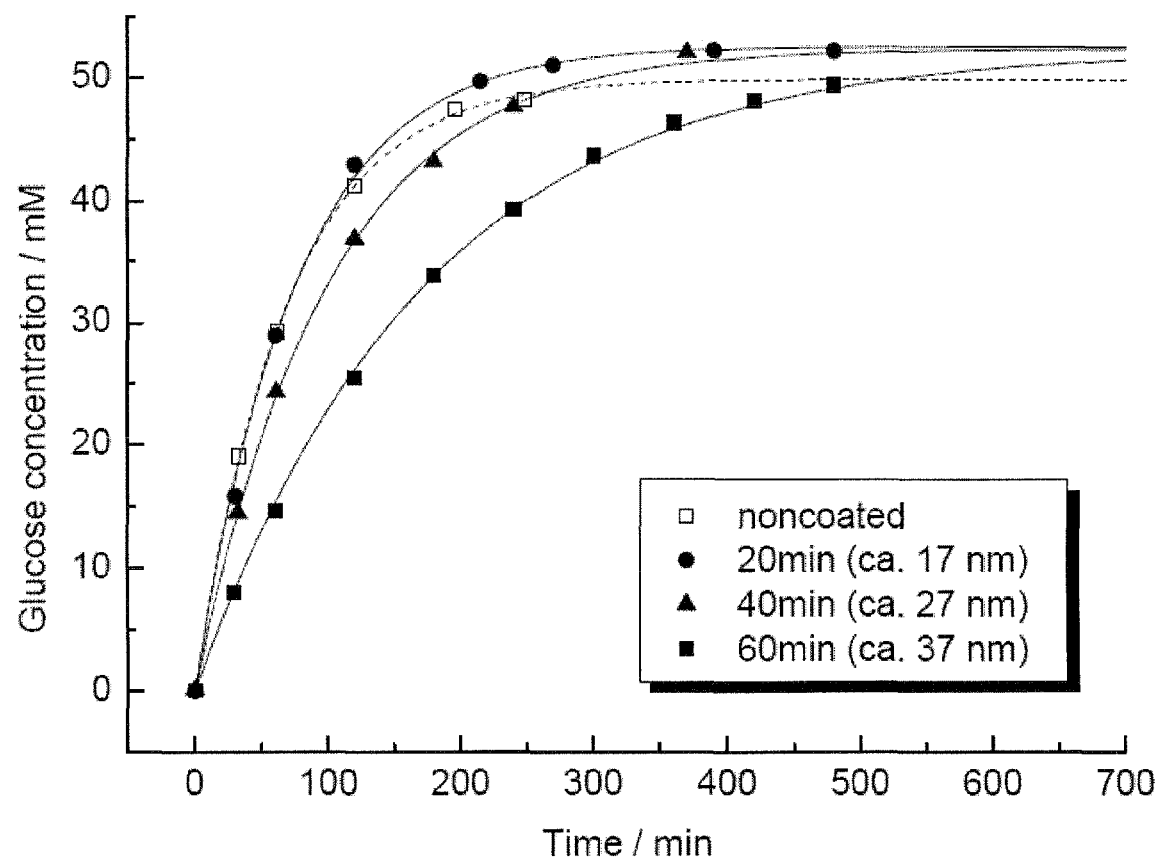

FIG. 4(a) shows a graphical representation of the glucose diffusion as a function of time through PPEGMA coated alumina membranes having PPEGMA coatings of various thicknesses. The results shown in FIG. 4(a) indicate that the glucose diffusion rate through the membrane can be controlled by controlling the thickness of the PPEGMA polymer brush layer.

Example 4(B): The diffusion of glucose and albumin across alumina membrane substrates with PPEGMA polymer brush coating obtained after polymerisation time of 120 minutes and 160 minutes produced according to Example 3 (initiator C), were evaluated.

Figure 4B:
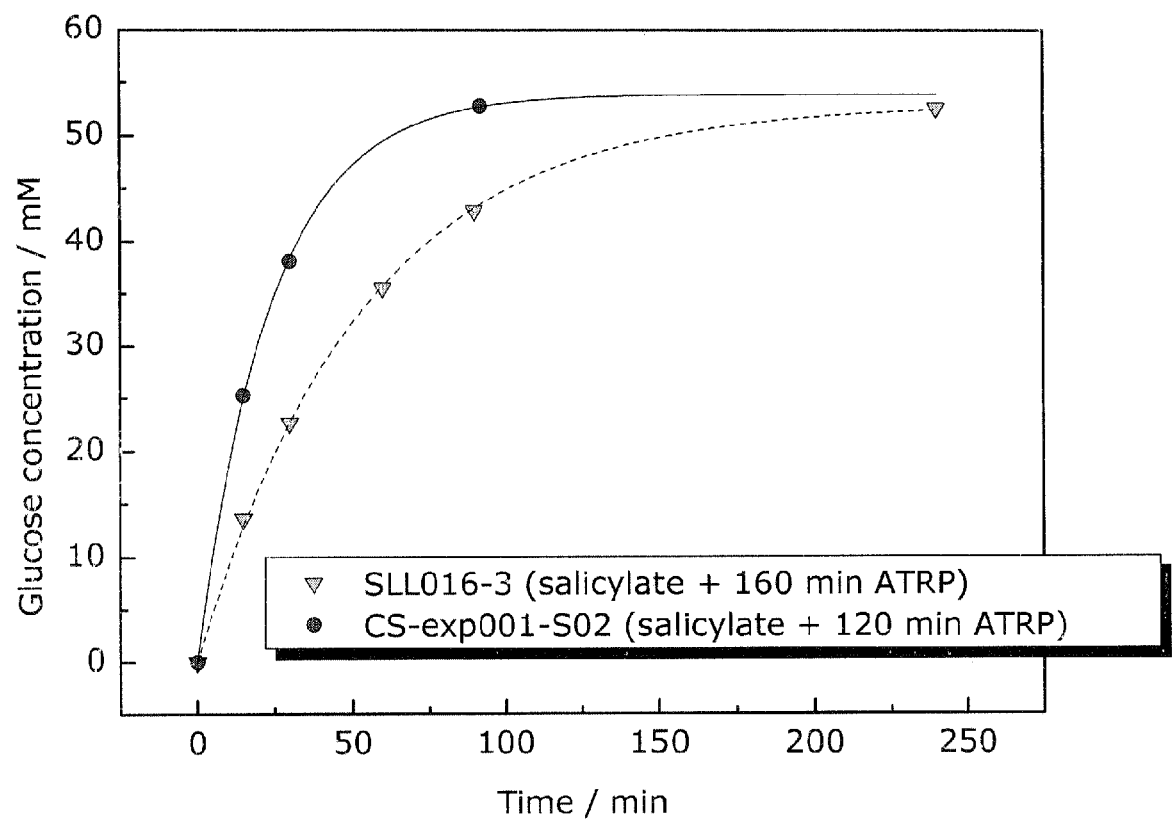

FIG. 4(b) shows a graphical representation of the glucose diffusion as a function of time through PPEGMA coated alumina membranes having PPEGMA coatings of various thicknesses. The results shown in FIG. 4(b) indicate that the glucose diffusion rate through the membrane can be controlled by controlling the thickness of the PPEGMA polymer brush layer.

For the albumin leakage/retention tests an aqueous solution containing 1%-bovine serum albumin (BSA) filled in one compartment of the test cell and a reference solution (no BSA) filled in the second compartment. Again, the aqueous solution in each compartment of the test cell was mixed by a magnetic stirrer. The test cell was observed for leakage of BSA over 48 hours. The leakage or retention of BSA was analysed by UV spectroscopy (USB4000-UV-VIS miniature Fiber Optic Spectrometer, Ocean Optics, Inc.), whereby leakage of albumin was detected by observance of a peak at the wavelength of 280 nm. The results of the albumin leakage/retention tests on PPEGMA coated alumina membranes prepared according to Example 1 are tabulated in table 1 below:

TABLE 1

| Coating growth time (min) | Coating thickness (nm) | Albumin retention (48 h test) |
|---|---|---|
| 0 | 0 | leakage |
| 20 | 17 | leakage |
| 40 | 27 | retention |
| 60 | 37 | retention |
| 180 | 75 | retention |

Similar results were obtained with the PPEGMA coated alumina membranes prepared according to Example 3.

The results as shown in FIGS. 4(a) and 4(b), and Table 1 indicate that the glucose diffusion time and the protein retention capability can be controlled by controlling the thickness of the PPEGMA brush coating layer. A decrease in the PPEGMA brush layer thickness leads to a reduction in selective permeability of the membrane with respect to preventing diffusion of proteins, while the glucose diffusion rate increases.

Example 5

Stability of PPEGMA$_{10}$ Brush Coating (A): Stability of PPEGMA polymer brush coating prepared according to Example 1 (initiator A).

Figure 5A:
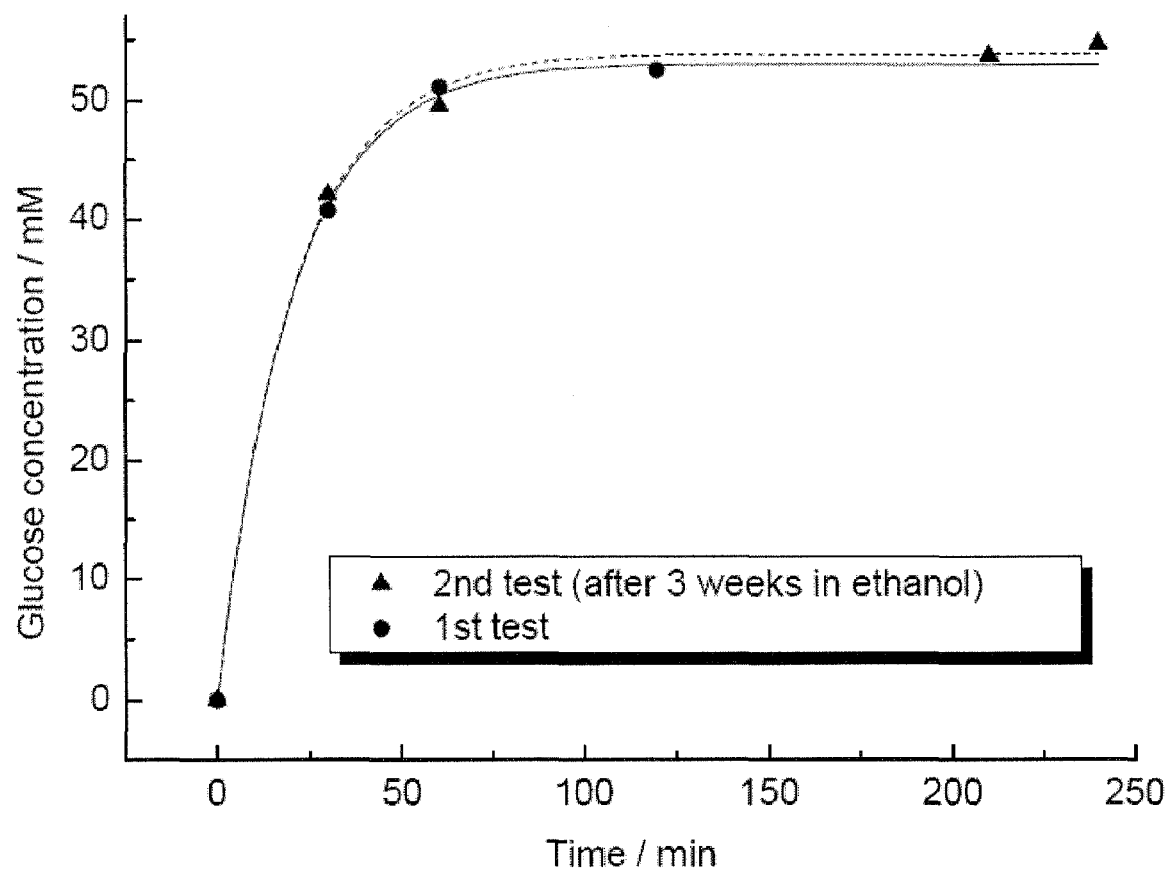

PPEGMA$_{10}$ polymer brush coated nanoporous alumina membranes prepared according to Example 1 were sterilized in hot ethanol (70° C.) for 2 h and then stored in ethanol (≧99.8%, Fluka) for 3 weeks at room temperature. Results of glucose diffusion tests, carried out according to the method detailed in Example 4, on the PPEGMA$_{10}$ polymer brush coated nanoporous alumina membranes before and after storage for 3 weeks in ethanol are shown in FIG. 5(a). No difference on the glucose diffusion behaviours through the coated membrane before and after having stored in ethanol has been observed. Albumin retention/leakage tests, carried out according to the method detailed in Example 4, also showed that protein retention capability has been maintained after storage.

(B): Stability of PPEGMA polymer brush coating prepared according to Example 3 (initiator C).

Figure 5B:
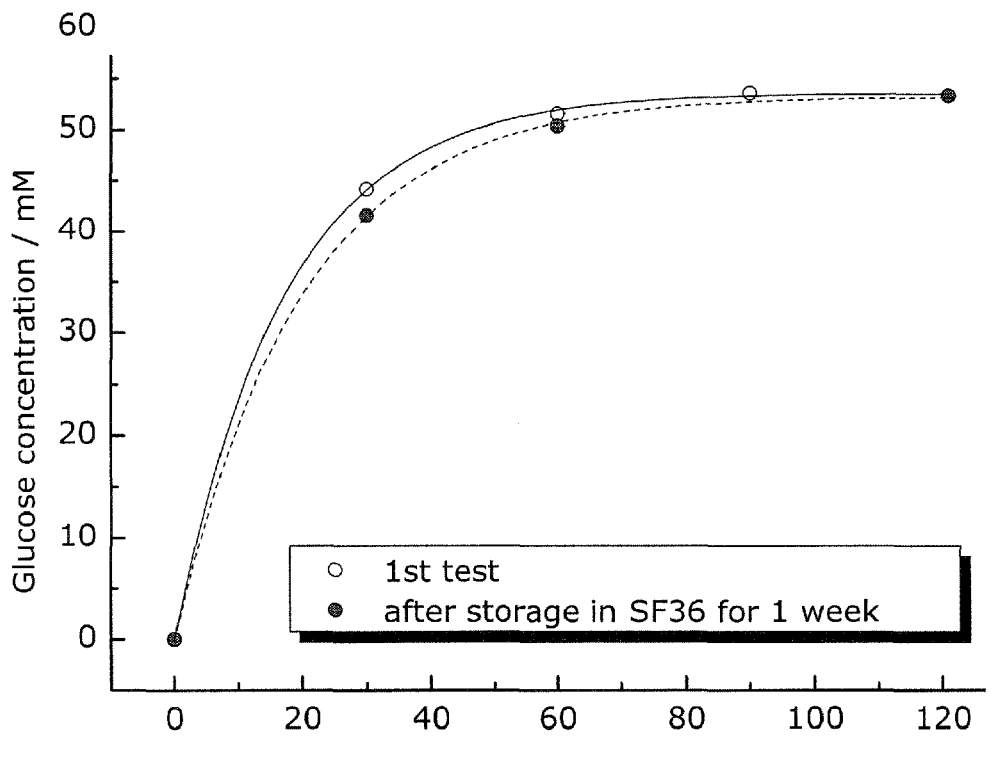
Figure 5C:
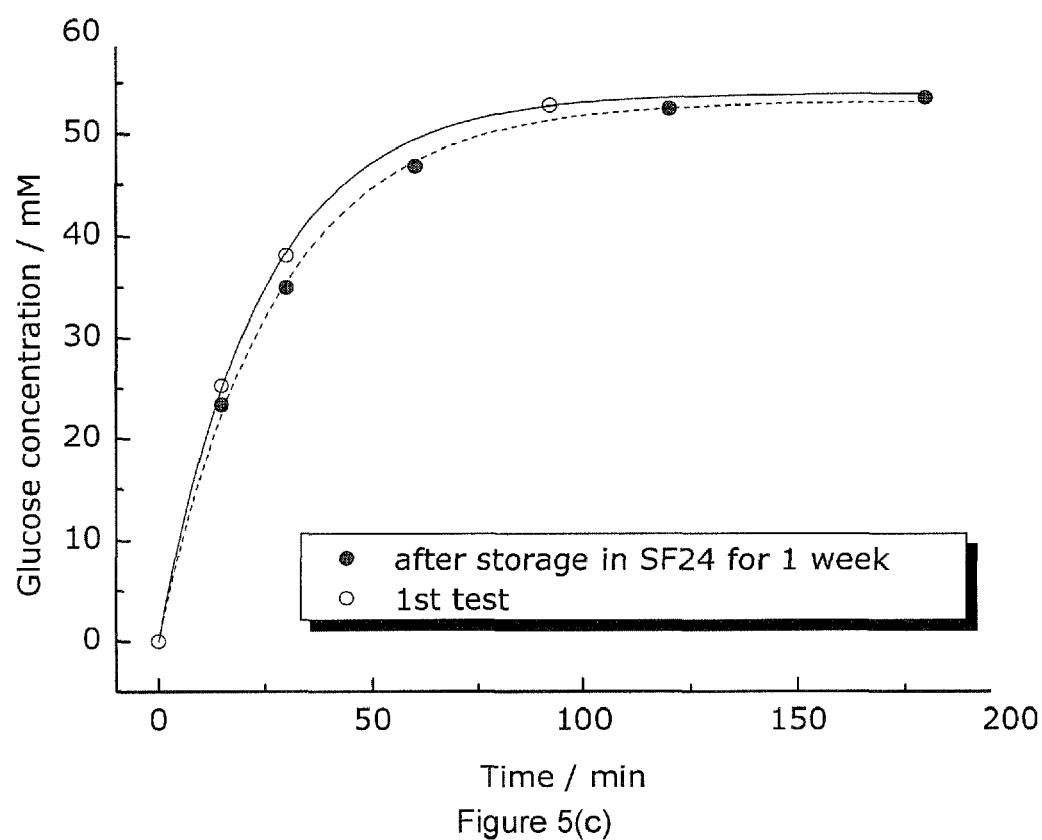

PPEGMA$_{10}$ polymer brush coated nanoporous alumina membranes prepared according to Example 3 were stored in Concanavalin A/Dextran buffered solution (0.6% ConA/3.0% Dextran for "SF36", results shown in FIG. 5(b), and 0.4% ConA/2.0% Dextran for "SF24", results shown in FIG. 5(c)), (Buffer solution: 10 mM TRIZMA (Tris(hydroxymethyl) aminoethane) pH7.4 (sourced from Sigma), 1 mM calcium chloride dehydrate, 1 mM Manganese(II) chloride tetrahydrate, 0.05% sodium azide, 2 mM-D-(+)-glucose anhydrous, 0.15 M sodium chloride) for one week at 25° C. The ConcanavalinA/Dextran buffered solutions correspond to models of a ConA/Dextran glucose sensitive solution suitable for use in an implantable glucose sensor device as described above. Results of glucose diffusion tests, carried out according to the method detailed in Example 4, on the PPEGMA$_{10}$ polymer brush coated nanoporous alumina membranes before and after storage for 1 week in ConA/Dextran buffered solution are shown in FIGS. 5(b) and 5(c). No significant difference in the glucose diffusion behaviours through the coated membrane before and after incubation was observed, indicating the stability of the PPEGMA$_{10}$ polymer brushes. Additionally, PPEGMA$_{10}$ polymer brush coated alumina membranes were sterilized using gamma radiations (Co$_{60}$, 30 kGy, for 50 hours). No modification was observed, indicating that the PPEGMA$_{10}$ polymer brush coated nanoporous alumina membrane was not damaged by gamma radiations.

The results shown in FIGS. 5(a), 5(b) and 5(c) illustrate good long-term stability properties of the polymer brush coated selectively permeable membranes of the invention, advantageous for many biomedical applications.

Example 6

In Vivo Evaluation of Bio-Compatibility

Samples of an alumina nanoporous substrate and a PPEGMA polymer brush coated nanoporous alumina substrate prepared according to Examples 1 and 3 were implanted into the backs of adult rats.

Example 6(A)—Coated nanoporous alumina substrates prepared according to Example 1 were implanted for a period of 10 days. Optical micrographs of the haematoxylin and eosin end sections of implant are shown in FIG. 6. Histological evaluation of haematoxylin and eosin stained sections showed that there is very little fibrous capsule present around the samples and the surrounding tissue is well vascularised, indicating good bio-compatibility of the membranes.

Example 6(B)—Membranes prepared according to Example 3 were implanted into the backs of adult rats for a period of 6 weeks. Similar results to those described above were obtained.

For each time point a PPEGMA polymer brush coated alumina membrane prepared according to Example 3 was implanted into the back skin of 4 rats.

After one week of implantation the wound healing process was not fully complete, but in 3 out of 4 rats the implantation site was clean. The scare of one was dirty and would appear to have been eaten by the rat. It was the only site where we detect blood under the membrane. The 3 other implantation sites had no blood or inflammation signs.

After 3 and 6 weeks of implantation, the wound healing process was complete and the scares were clean and nice. All of the implanted rats showed no signs of chronic inflammation.

After 12 weeks, the scares were not visible.

Figure 6A:
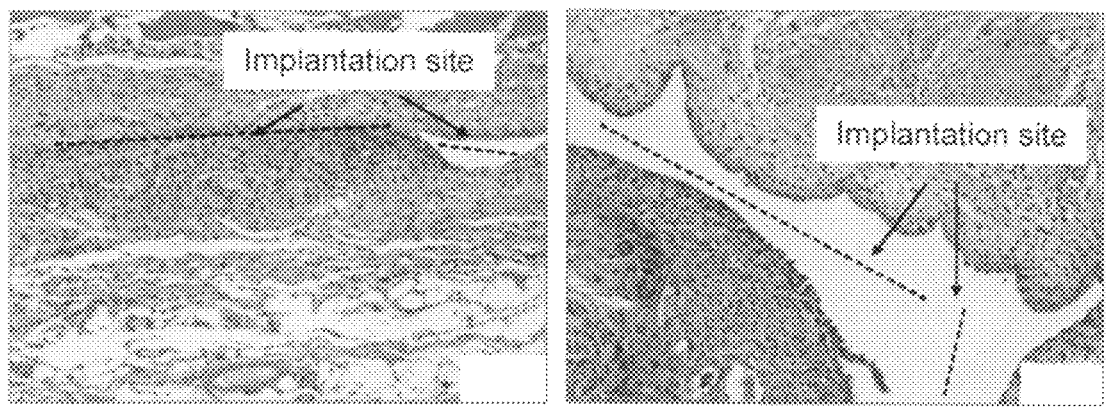
Figure 6B:
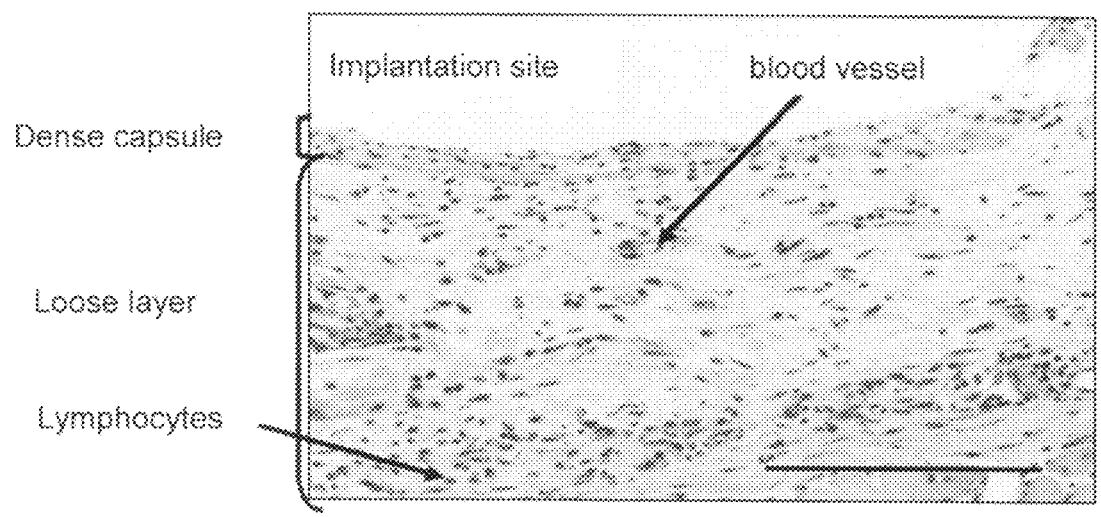

Skin samples containing the membranes were dissected and fixed overnight in 4% paraformaldehyde. The alumina membrane was then removed and the skin processed to paraffin for histology. 4 μm sections of the implantation sites were stained with haematoxylin and eosin, or Masson's Trichrome (FIGS. 6b to 6d).

After 1 week, the tissue around the membrane was composed of a thin and dense cellular capsule next to the membrane sample (5-20 μm) and a looser layer formed by collagen up to 200 μm thick (stained by Masson's Trichrome). Optical micrographs of the haematoxylin and eosin end sections of implant, taken at high resolution (×100), are shown in FIG. 6(b). In the collagen tissue, was detected the formation of small blood vessels heterogeneously distributed around the implantation site. Furthermore lymphocytes were present in moderate amount showing a mild inflammation. The number of lymphocytes was variable among the 4 implanted rats.

Figure 6C:
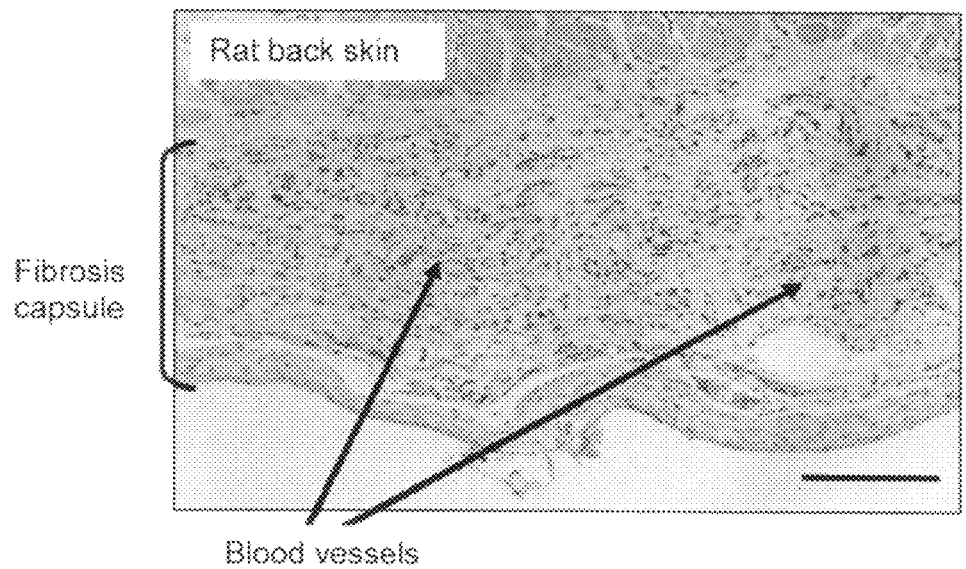

An optical micrograph of a haematoxylin and eosin end section of implant after 3 weeks is shown in FIG. 6(c). Histological evaluation of the haematoxylin and eosin stained sections showed that after 3 weeks the dense capsule close to the membrane was thicker (50 μm). However blood vessels were present and no lymphocytes.

Figure 6D:
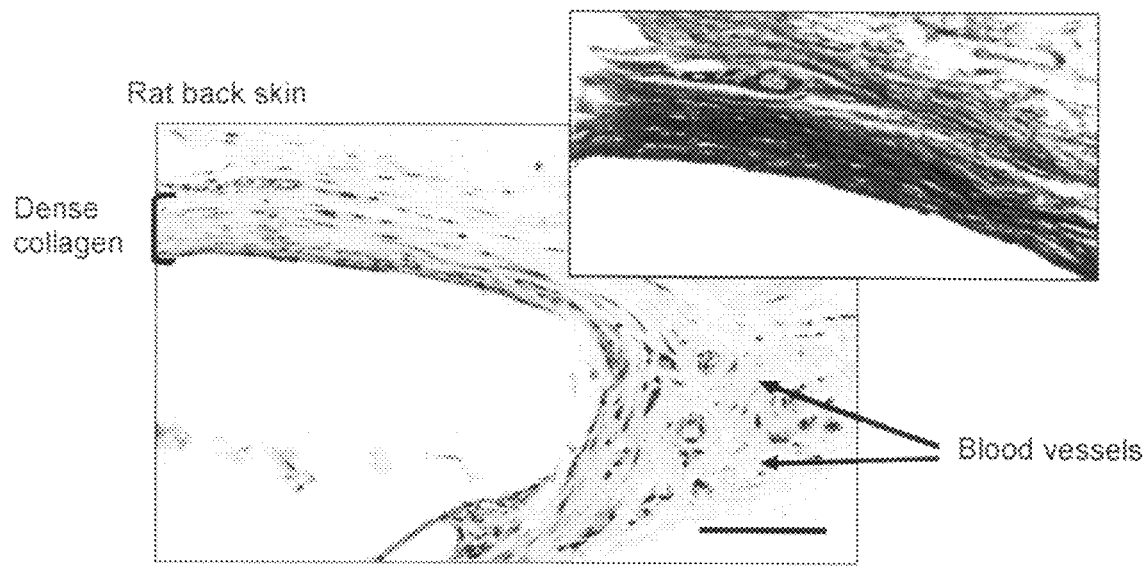

Optical micrographs of a haematoxylin and eosin end section, and a Masson—s Trichrome stained section, after 6 weeks are shown in FIG. 6(d) (haematoxylin and eosin stained section—lower panel, and Masson's Trichrome stained section—upper panel). Histological evaluation of the haematoxylin and eosin stained sections, and Masson's trichrome stained sections, showed that after 6 weeks the fibrosis capsule had not increased in size and was mainly composed of collagen. Blood vessels were present but no lymphocytes. Thereby indicating good bio-compatibility of the membranes.

We claim:

1. An implantable analyte sensor comprising a biointerface membrane permitting selective diffusion of an analyte therethrough, said membrane comprising a nanoporous substrate and a coating on said nanoporous substrate restricting a pore size of the nanoporous substrate, said coating comprising a plurality of bio-compatible polymer chains, whereby each polymer chain is covalently attached at one chain end thereof to a surface of the nanoporous substrate via a 5-(2-bromo-2-methylpropanamido)-2-hydroxybenzoic acid group and whereby the polymer chains are formed by a surface-initiated controlled polymerization process from the nanoporous substrate.

2. The sensor according to claim 1, wherein the sensor is a glucose sensor.

3. The sensor according to claim 1, wherein the polymer chains are formed by polymerisation of one or more monomer selected from the group consisting of 2-hydroxyethyl methacrylate, glycidyl methacrylate, (polyethylene glycol) methacrylate, (polyethylene glycol) methylether methacrylate, ethylene glycol dimethacrylate, and poly(ethylene glycol)dimethacrylate.

4. The sensor according to claim 3, wherein the polymer chains are composed of poly(poly(ethylene glycol) methacrylate) chains.

5. The sensor according to claim 1, wherein the substrate is a nanoporous alumina substrate.

6. The sensor according to claim 5, wherein the nanoporous substrate has a pore size of at least 20 nm and no more than 100 nm.

7. The sensor according to claim 1, wherein the nanoporous substrate has a pore size of at least 2 nm and no more than 200 nm.

8. The sensor according to claim 1, wherein the coating of the nanoporous substrate has a thickness of at least 10 nm and no more than 100 nm.

9. The sensor according to claim 1, wherein the membrane has a pore size in the range of from 0.1 nm to 10 nm.

10. The implantable analyte sensor according to claim 1, wherein said polymer chains comprise water soluble monomers.

11. A bio-interface membrane for an analyte sensor permitting selective diffusion of an analyte therethrough comprising:

a nanoporous substrate and a coating on said nanoporous substrate, said coating comprising a plurality of bio-compatible polymer chains, whereby each polymer chain is covalently attached at one chain end thereof to a surface of the nanoporous substrate via a 5-(2-bromo-2-methylpropanamido)-2-hydroxybenzoic acid group and whereby the polymer chains are formed by a surface-initiated controlled polymerization process from the nanoporous substrate, said coating restricting a pore size of the pores of the nanoporous substrate so as to provide selective diffusion of the analyte through the membrane.

12. The membrane according to claim 11, wherein the analyte is glucose.

13. The membrane according to claim 11, wherein the polymer chains are formed by polymerisation of one or more monomer selected from the group consisting of 2-hydroxyethyl methacrylate, glycidyl methacrylate, (polyethylene glycol) methacrylate, (polyethylene glycol) methylether methacrylate, ethylene glycol dimethacrylate, and poly(ethylene glycol)dimethacrylate.

14. The membrane according to claim 13, wherein the polymer chains are composed of poly(poly(ethylene glycol) methacrylate) chains.

15. The membrane according to claim 11, wherein the substrate is a nanoporous alumina substrate.

16. The membrane according to claim 15, wherein the nanoporous substrate has a pore size of at least 20 nm and no more than 100 nm.

17. The membrane according to claim 11, wherein the nanoporous substrate has a pore size of at least 2 nm and no more than 200 nm.

18. The membrane according to claim 11, wherein the coating of the nanoporous substrate has a thickness of at least 10 nm and no more than 100 nm.

19. The membrane according to claim 11, wherein the membrane has a pore size in the range of from 0.1 nm to 10 nm.

20. The membrane according to claim 11, wherein said polymer chains comprise water soluble monomers.

21. A method for the preparation of a selectively permeable biointerface membrane for use in an analyte sensor, comprising chemically binding a monolayer of an initiator group onto a surface of a nanoporous substrate, and subsequently carrying out a polymerisation by a surface-initiated controlled polymerization process from the monolayer of said initiator group to form a coating on the nanoporous substrate comprising a plurality of bio-compatible polymer chains, whereby each polymer chain is attached at one chain end thereof to a surface of the nanoporous substrate via a 5-(2-bromo-2-methylpropanamido)-2-hydroxybenzoic acid group, said coating restricting a pore size of the nanoporous substrate so as to provide selective diffusion of an analyte through the membrane, wherein said surface-initiated controlled polymerization process comprises surface initiated atom transfer radical polymerisation.

22. The method according to claim 21, wherein the nanoporous substrate is a nanoporous alumina substrate.

23. The method according to claim 22, wherein the nanoporous substrate has a pore size of at least 20 nm and no more than 100 nm.

24. The method according to claim 21, wherein the nanoporous substrate has a pore size of at least 2 nm and no more than 200 nm.

25. The method according to claim 21, wherein the coating of the nanoporous substrate has a thickness of at least 10 nm and no more than 100 nm.

26. The method according to claim 21, wherein the thickness of the nanoporous coating is controlled by controlling the length of time of the polymerisation.

27. The method according to claim 21, wherein the polymer chains are formed by polymerisation of one or more monomer selected from the group consisting of 2-hydroxyethyl methacrylate, glycidyl methacrylate, (polyethylene glycol) methacrylate, (polyethylene glycol) methylether methacrylate, ethylene glycol dimethacrylate, and poly(ethylene glycol)dimethacrylate.

28. The method according to claim 27, wherein the polymer chains are composed of poly(poly(ethylene glycol) methacrylate) chains.

29. The method according to claim 21, wherein said polymer chains comprise water soluble monomers.

* * * * *